(12) United States Patent
Adinolfi (10) Patent No.: US 10,722,111 B2
(45) Date of Patent: Jul. 28, 2020

(54) OPTICAL TROCAR ASSEMBLY

(71) Applicant: Covidien LP, Mansfield, MA (US)

(72) Inventor: Amanda Adinolfi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 240 days.

(21) Appl. No.: 15/919,854

(22) Filed: Mar. 13, 2018

(65) Prior Publication Data
US 2019/0282081 A1 Sep. 19, 2019

(51) Int. Cl.
| A61B 1/32 | (2006.01) |
| A61B 1/313 | (2006.01) |
| A61B 17/02 | (2006.01) |
| A61B 17/34 | (2006.01) |
| A61B 17/32 | (2006.01) |
| A61B 17/00 | (2006.01) |
| A61B 90/00 | (2016.01) |

(52) U.S. Cl.
CPC .............. *A61B 1/32* (2013.01); *A61B 1/3132* (2013.01); *A61B 17/0218* (2013.01); *A61B 17/3417* (2013.01); *A61B 17/3423* (2013.01); *A61B 90/361* (2016.02); *A61B 2017/00907* (2013.01); *A61B 2017/320044* (2013.01); *A61B 2017/347* (2013.01); *A61B 2017/3454* (2013.01)

(58) Field of Classification Search
CPC ..... A61B 1/32; A61B 1/3132; A61B 17/3423; A61B 17/3417
See application file for complete search history.

(56) References Cited

U.S. PATENT DOCUMENTS

| 5,342,315 A * | 8/1994 | Rowe ................. A61B 17/3462 |
| | | 604/167.06 |
| 5,674,181 A | 10/1997 | Iida |
| 5,685,823 A | 11/1997 | Ito et al. |
| 5,725,477 A | 3/1998 | Yasui et al. |

(Continued)

FOREIGN PATENT DOCUMENTS

| CN | 101259030 A | 9/2008 |
| EP | 0664992 A1 | 8/1995 |

(Continued)

OTHER PUBLICATIONS

Supplementary European Search Report issued in corresponding EP application No. 12840970.3 dated Jul. 8, 2015.

(Continued)

*Primary Examiner* — Zade Coley
(74) *Attorney, Agent, or Firm* — Carter, DeLuca & Farrell LLP (57) ABSTRACT

An optical trocar assembly includes an obturator assembly and a cannula assembly configured for receipt of the obturator assembly. The obturator assembly has a retention member disposed within a cavity defined in an obturator housing of the obturator assembly. The retention member has a main body defining an opening dimensioned for receipt of a surgical instrument. The retention member has a plurality of first sections formed in the main body and circumferentially disposed about the opening. The sections have a reduced thickness relative to the main body to facilitate flexing of the retention member during insertion of a surgical instrument into the opening.

20 Claims, 6 Drawing Sheets

(56) References Cited

U.S. PATENT DOCUMENTS

| | | | |
|---|---|---|---|
| 5,743,884 A * | 4/1998 | Hasson | A61B 17/3462 137/247.17 |
| 5,817,061 A | 10/1998 | Goodwin et al. | |
| 6,755,782 B2 | 6/2004 | Ogawa | |
| 7,485,092 B1 | 2/2009 | Stewart et al. | |
| 9,351,717 B2 * | 5/2016 | Widenhouse | A61B 17/0218 |
| 2001/0044570 A1 | 11/2001 | Ouchi et al. | |
| 2002/0035311 A1 | 3/2002 | Ouchi | |
| 2005/0033237 A1 | 2/2005 | Fentress et al. | |
| 2005/0065543 A1 | 3/2005 | Kahle et al. | |
| 2005/0107816 A1 | 5/2005 | Pingleton et al. | |
| 2005/0149096 A1 | 7/2005 | Hilal et al. | |
| 2005/0272975 A1 | 12/2005 | McWeeney et al. | |
| 2005/0288622 A1 | 12/2005 | Albrecht et al. | |
| 2006/0047284 A1 | 3/2006 | Gresham | |
| 2006/0224174 A1 | 10/2006 | Smith et al. | |
| 2007/0129719 A1 | 6/2007 | Kendale et al. | |
| 2007/0260121 A1 | 11/2007 | Bakos et al. | |
| 2008/0086160 A1 | 4/2008 | Mastri et al. | |
| 2008/0300617 A1 | 12/2008 | Smith | |
| 2009/0023986 A1 | 1/2009 | Stewart et al. | |
| 2010/0016664 A1 | 1/2010 | Viola | |
| 2010/0063450 A1 | 3/2010 | Smith et al. | |
| 2010/0318112 A1 | 12/2010 | Smith | |
| 2011/0288483 A1 * | 11/2011 | Zhou | A61B 17/3462 604/167.03 |
| 2011/0313242 A1 | 12/2011 | Surti | |
| 2014/0235946 A1 * | 8/2014 | Smith | A61B 17/3417 600/114 |
| 2014/0249371 A1 * | 9/2014 | Fischvogt | A61B 17/3494 600/114 |
| 2015/0031958 A1 * | 1/2015 | Kleyman | A61B 17/3423 600/204 |
| 2015/0216560 A1 * | 8/2015 | Holsten | A61B 17/3462 600/204 |
| 2016/0081715 A1 * | 3/2016 | Kleyman | A61B 17/3423 600/204 |

FOREIGN PATENT DOCUMENTS

| | | | |
|---|---|---|---|
| EP | 2000099 A2 | 12/2008 | |
| JP | H08266548 A | 10/1996 | |
| JP | 2005503230 A | 2/2005 | |
| JP | 2006289083 A | 10/2006 | |
| JP | 2007516737 A | 6/2007 | |
| JP | 2008504886 A | 2/2008 | |
| JP | 2008296027 A | 12/2008 | |
| JP | 2011125709 A | 6/2011 | |
| WO | 9952577 A1 | 10/1999 | |
| WO | WO-9952577 A1 * | 10/1999 | A61B 17/3498 |
| WO | 2008103400 A2 | 8/2008 | |
| WO | 2011044118 A1 | 4/2011 | |

OTHER PUBLICATIONS

Examination Report issued in corresponding Australian Patent Application No. 2012326322 dated May 17, 2016.

Japanese Office Action dated Aug. 1, 2016 in corresponding Japanese Patent Application No. 2014-537147, together with English translation, 12 pages.

Japanese Notice of Allowance dated Dec. 7, 2016 in corresponding Japanese Patent Application No. 2014-537147, together with English summary, 5 pages.

Examination Report No. 2 in corresponding Australian Application No. 2012326322, dated Feb. 9, 2017, 4 pages.

Australian Examination Report issued in corresponding Australian Patent Application No. 2017216514 dated Nov. 30, 2017.

International Search Report for PCT/US12/60392, dated Mar. 21, 2013 (3 pages).

European Search Report, dated Jul. 8, 2019, corresponding to corresponding European Application No. 19162107.7, 10 pages.

* cited by examiner

FIG. 9

OPTICAL TROCAR ASSEMBLY

BACKGROUND

Technical Field

The present disclosure relates to a trocar assembly for use in minimally invasive surgical procedures, such as endoscopic or laparoscopic type procedures.

Background of Related Art

Minimally invasive procedures are continually increasing in number and variation. Forming a relatively small diameter temporary pathway to the surgical site is a key feature of most minimally invasive surgical procedures. The most common method of providing such a pathway is by inserting a trocar assembly through the skin. In many procedures, the trocar assembly is inserted into an insufflated body cavity of a patient. In such procedures, trocar assemblies with seal mechanisms are utilized to provide the necessary pathway to the surgical site while minimizing leakage of insufflation gases.

Trocar assemblies typically include an obturator and a cannula. The cannula, having the obturator inserted therethrough, is directed through the skin to access a body cavity. Once the body cavity is accessed, laparoscopic or arthroscopic surgery and endoscopic procedures may be performed. With the cannula providing access to the body cavity, a surgical instrument (e.g., an endoscope or a laparoscope) may be guided into the body cavity through the cannula.

During a surgical procedure, inadvertent rotation of the surgical instrument within and relative to the trocar assembly is undesirable. However, it is advantageous to allow for manipulation of the surgical instrument upon the intentional application of a threshold amount of force thereto. Accordingly, a need exists for a trocar assembly that provides the appropriate amount of stabilization of a surgical instrument received therein.

SUMMARY

In an aspect of the present disclosure, an obturator assembly is provided and includes an obturator housing defining a cavity therein, an obturator shaft extending distally from the housing, and a retention member disposed within the cavity of the obturator housing. The retention member has a main body and a plurality of first sections formed in the main body. The main body has a first thickness and defines an opening dimensioned for receipt of a surgical instrument. The first sections are circumferentially disposed about the opening and have a second thickness that is less than the first thickness of the main body to facilitate flexing of the retention member during insertion of a surgical instrument into the opening.

In some aspects, each of the first sections may extend radially outward from the opening.

In some aspects, each of the first sections may extend from an inner peripheral surface of the main body of the retention member radially outward toward an outer peripheral surface of the main body of the retention member.

In some aspects, each of the first sections may have an outer edge disposed inwardly of the outer peripheral surface.

In some aspects, each of the first sections may have an outer edge coincident with the outer peripheral surface.

In some aspects, each of the first sections may include a bottom surface, and a transition surface extending transversely between the bottom surface and one of an upper surface or a lower surface of the main body of the retention member.

In some aspects, one or more of the first sections has a triangular configuration or a squared configuration.

In some aspects, each of the first sections may be a depression formed in an upper surface or a lower surface of the main body of the retention member.

In some aspects, the upper and lower surfaces of the main body of the retention member may be planar.

In some aspects, the retention member may have a circular configuration.

In some aspects, the opening of the retention member may be aligned with a central longitudinal axis defined by the obturator shaft.

In some aspects, the retention member may be fabricated from a unitary piece of elastic material. The elastic material may be rubber and/or silicone.

In another aspect of the present disclosure, an optical trocar system is provided and includes the obturator assembly and a cannula assembly configured to receive the obturator shaft of the obturator assembly therein.

Further scope of applicability of the present disclosure will become apparent from the detailed description given hereinafter. However, it should be understood that the detailed description and specific examples, while indicating embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

The figures depict embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The present disclosure, in accordance with various example embodiments thereof, relates to an optical trocar system that provides access to a body cavity through an anatomical, e.g., abdominal, wall. It should be noted that, for the purposes of this description, the term optical trocar system may be used herein synonymously with the term visual obturator system. Advantageously, the optical trocar system of the present disclosure, in accordance with various embodiments thereof, includes a retention member designed to stabilize a surgical instrument (e.g., an endoscope or a laparoscope) relative to and within the optical trocar system. The retention member may be constructed from a unitary piece of elastomeric material and have a plurality of reduced-thickness sections disposed around a central opening thereof. The reduced-thickness sections allow for the retention member to flex upon receipt of a surgical instrument through the central opening. Disposed between the reduced-thickness sections are thicker sections that assist in stabilizing the surgical instrument within the central opening by inhibiting rotational movement and axial motion thereof during use.

Figure 1:
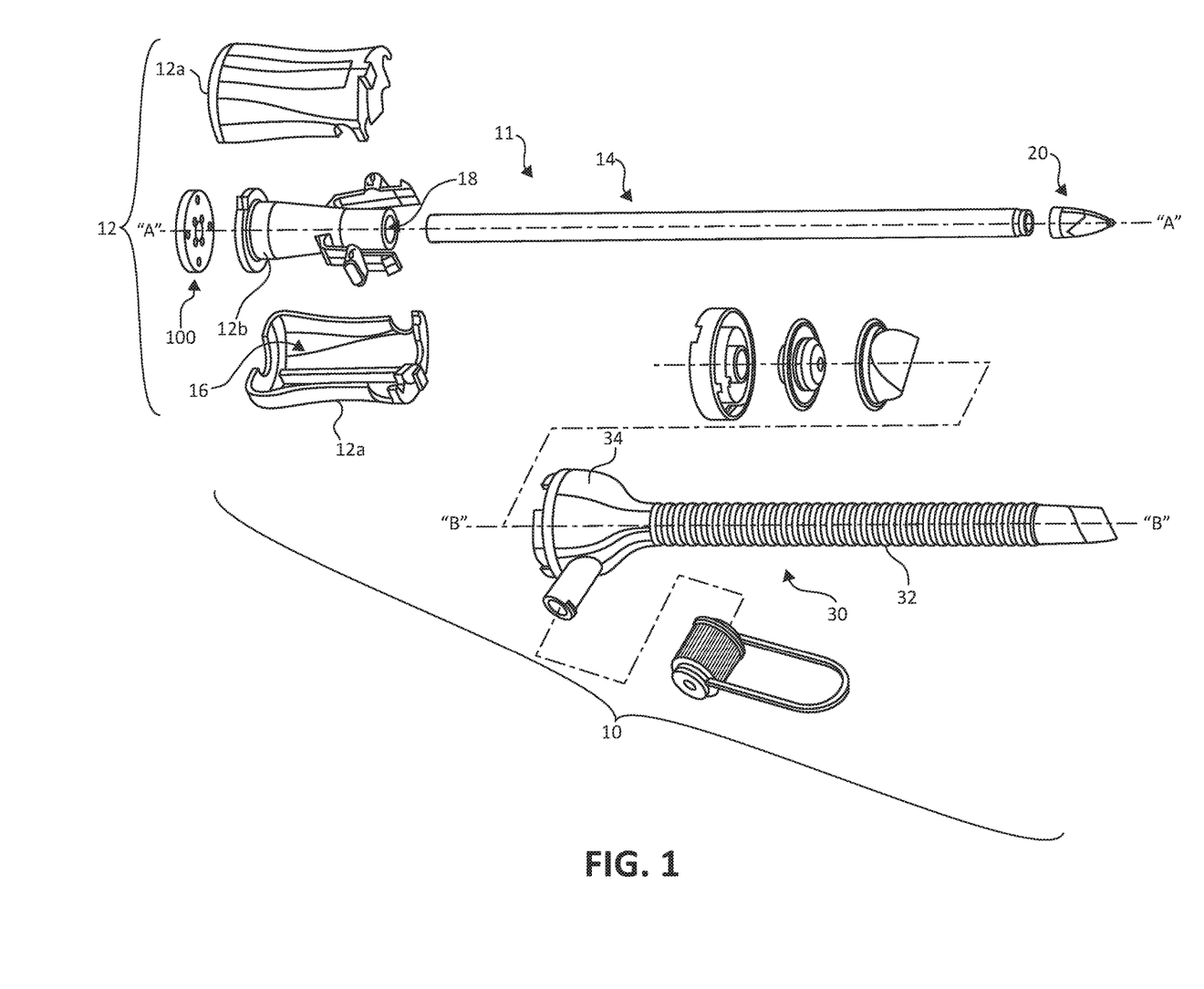
FIG. 1 is a perspective view, with parts separated, of an exemplary embodiment of a trocar assembly including an obturator assembly and a cannula assembly.
Figure 2:
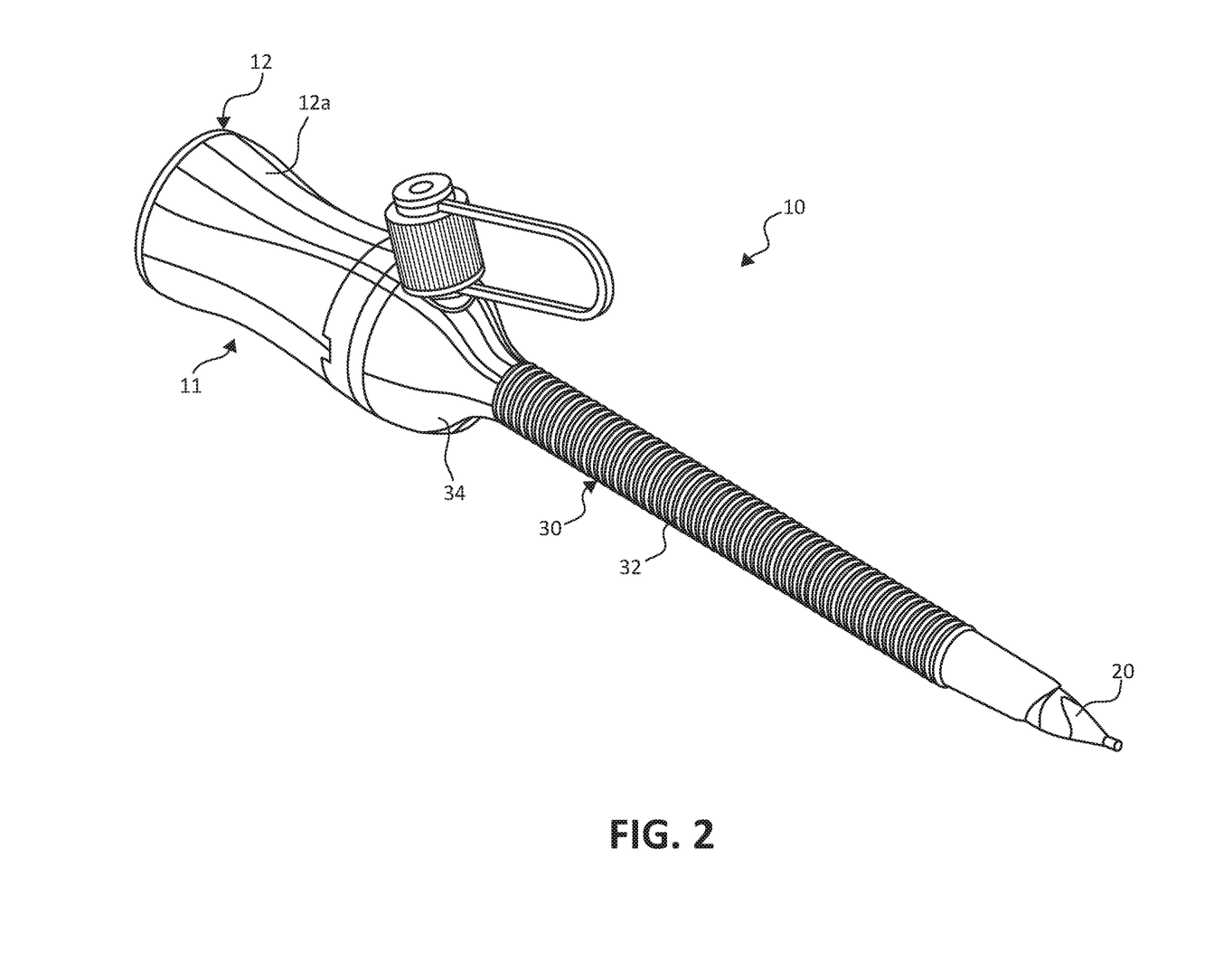
FIG. 2 is a side perspective view of the trocar assembly of FIG. 1 in an assembled state.
Figure 3:
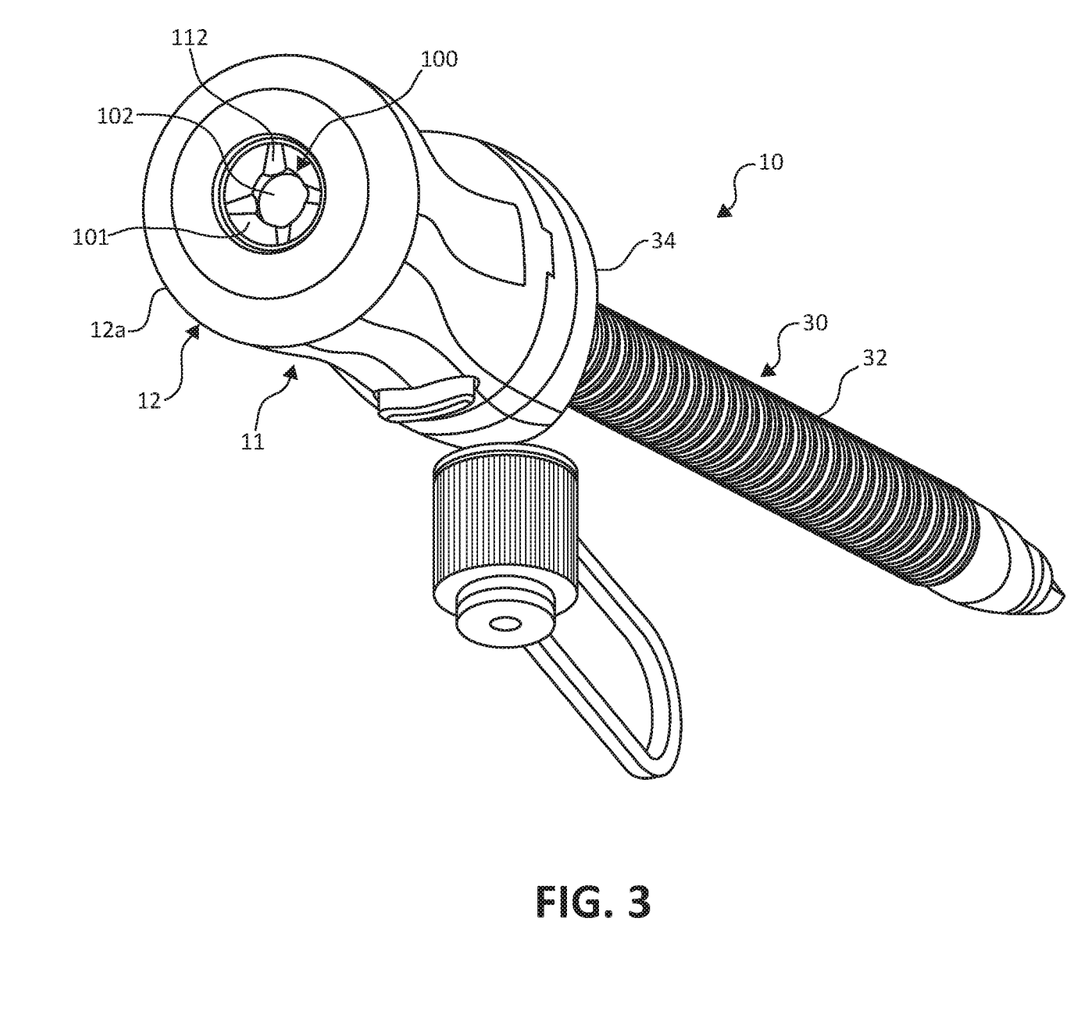
FIG. 3 is a top perspective view of the trocar assembly of FIG. 2 in the assembled state.

Referring now to FIGS. 1-3, there is illustrated an optical trocar, e.g., visual obturator, system or assembly 10 in accordance with an embodiment of the present disclosure. The visual obturator system 10 is intended for separating tissue planes in an endoscopic, e.g., laparoscopic, surgical procedure, and, is particularly suitable for the blunt dissection of the abdominal lining during a surgical procedure. The visual obturator system 10 is adapted to receive a surgical instrument, such as, for example, an endoscope, to permit viewing of tissue during the insertion and advancement of the visual obturator system 10 toward the operative site.

In accordance with the embodiment shown, the visual obturator system 10 generally includes an obturator assembly 11 and a cannula assembly 30 which at least partially receives the obturator assembly 11. The cannula assembly 30 of the visual obturator system 10 includes a clear elongated portion 32, defining a longitudinal axis "B-B," and a head 34 monolithically formed with or connected to a proximal end portion of the elongated portion 32.

The obturator assembly 11 of the visual obturator system 10 includes an obturator housing assembly 12 disposed in mechanical cooperation with an elongated obturator shaft 14 of the obturator assembly 11. The obturator housing assembly 12 includes an outer housing 12a, and an inner housing 12b supported on a proximal end portion of the elongated obturator shaft 14. The outer housing 12a may be constructed from two half-sections joined to one another. The outer housing 12a defines a cavity 16 therein in which the inner housing 12b is situated. The inner housing 12b defines a central passageway 18 extending longitudinally therethrough that is coaxial with a longitudinal axis "A-A" defined by the elongated obturator shaft 14. The elongated obturator shaft 14 extends distally from the obturator housing assembly 12 and may be rigid, e.g., metal. The elongated obturator shaft 14 may be attached, e.g., by over molding thereto, at its proximal end portion to the obturator housing assembly 12 and at its distal end portion to an optical member 20.

The optical member 20 may be fabricated from a polymeric material, e.g., LEXAN, and is transparent, or at least semi-transparent, to permit passage of light rays. During assembly, the optical member 20 may be over-molded onto the distal end portion of the metal obturator shaft 14 to connect the components. The optical member 20 defines an internal chamfered or sloped surface (not explicitly shown) which is obliquely arranged relative to the longitudinal axis A-A. During use, the chamfered surface of the optical member 20 is directly engaged by the outermost periphery of a distal end of an endoscope (not shown), such that light transmitted from regions of the endoscope travel radially within the outer periphery across an air gap prior to being received by the chamfered or sloped surface of the optical member 20. The optical member 20 permits the passage of light rays to enable viewing (by the endoscope) of tissue adjacent the optical member 20 during the insertion and/or advancement of the visual obturator system 10 through the tissue.

Figure 4:
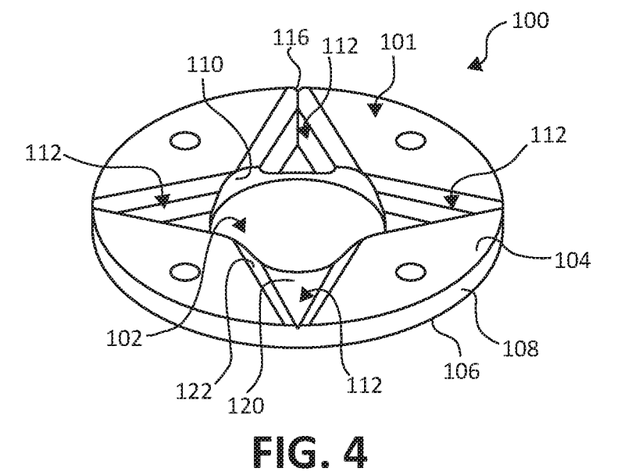
FIG. 4 is a top perspective view of an exemplary embodiment of a retention member for receipt in the obturator assembly of FIG. 1.
Figure 5:
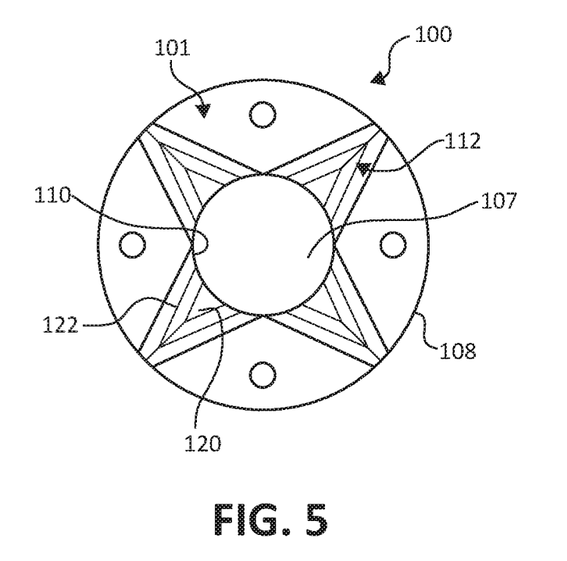
FIG. 5 is a top view of the retention member of FIG. 4.

With specific reference to FIGS. 3-5, the obturator assembly 11 further includes a retention member 100 disposed between the outer and inner housings 12a, 12b of the obturator housing assembly 12 and within the cavity 16 (FIG. 1) of the obturator housing assembly 12. The retention member 100 includes a main body 101 that defines a central opening 102 coaxially aligned with each of the passageway 18 (FIG. 1) of the inner housing 12b, the longitudinal axis A-A of the elongated obturator shaft 14, and the longitudinal axis B-B of the elongated portion 32 of the cannula assembly 30. The central opening 102 is dimensioned to receive a surgical instrument therethrough. The retention member 100 is constructed of a unitary piece of elastomeric material, such as an elastomer (e.g., rubber or silicone), and is adapted to engage an outer surface of a surgical instrument to assist in retaining the relative positioning of the surgical instrument within the optical trocar system 10.

The retention member 100 may have a generally planar, disc-shaped configuration. In some embodiments, the retention member 100 may assume any suitable configuration such as squared or triangular. The main body 101 of the retention member 100 has an upper surface 104, a lower surface 106, an outer peripheral surface 108, and an inner peripheral surface 110 that defines the central opening 102. The main body 101 defines a first thickness between the upper and lower surfaces 104, 106 thereof.

The retention member 100 further includes a plurality of first sections 112 formed in the main body 101 of the retention member 100. The first sections are circumferentially disposed about the opening 102 in the main body 101 of the retention member 100. The first sections 112 may be equally circumferentially spaced from one another about the opening 102 or unevenly circumferentially spaced about the opening 102. The first sections 112 may be depressions formed in the upper surface 104 of the main body 101 of the retention member 100, such that the first sections 112 have a reduced thickness relative to the main body 101 of the retention member 100.

In embodiments, the first sections 112 may have a reduced thickness relative to the entire main body 101 of the retention member 100 or only portions thereof. In embodiments, the first sections or depressions 112 may be formed in one or both of the upper and lower surfaces 104, 106 of the main body 101 of the retention member 100. In still other embodiments, rather than having a reduced thickness, the first sections 112 may have the same thickness as the remainder of the main body 101 of the retention member 100, but be fabricated from a relatively more flexible material than the main body 101. The first sections 112 are configured to permit flexure of the retention member 100 and enlargement of the central opening 102 upon insertion of a surgical instrument.

In some embodiments, only the inner peripheral surface 110 of the retention member 100 has a reduced thickness relative to the remainder of the retention member 100. It is contemplated that the first sections 112 may be disposed on only one side of the retention member 100.

Figure 6:
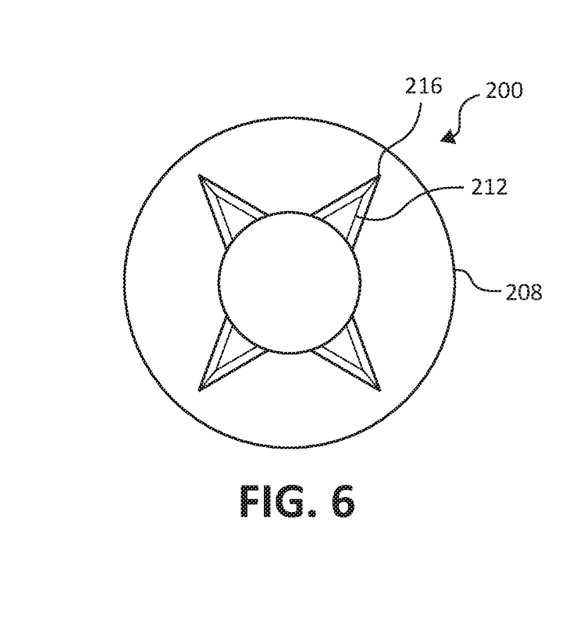
FIG. 6 is a top view of another embodiment of a retention member for receipt in the obturator assembly of FIG. 1.

The first sections 112 extend radially outward from the inner peripheral surface 110 of the main body 101 of the retention member 100 toward the outer peripheral surface 108 of the main body 101 of the retention member 100. The first sections 112 may each have an outer edge 116 coincident with the outer peripheral surface 108. In another embodiment of a retention member 200, shown in FIG. 6, the outer edge 216 of the first sections 212 may be disposed radially inward of the outer peripheral surface 208 of the retention member 200.

Figure 7:
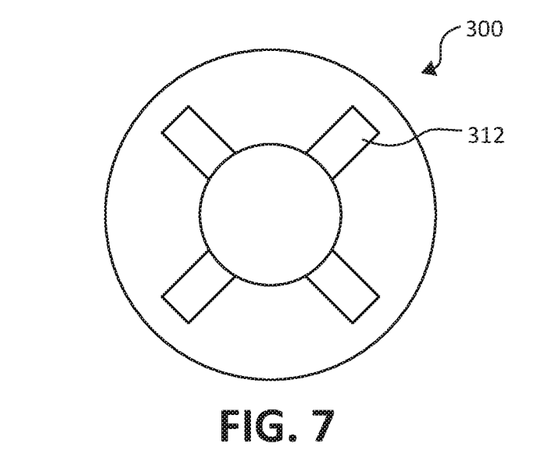
FIG. 7 is a top view of yet another embodiment of a retention member for receipt in the obturator assembly of FIG. 1.

With continued reference to FIGS. 3-5, each of the first sections 112 has a triangular configuration, wherein a base of each the first sections 112 is disposed adjacent the inner peripheral surface 110, and an apex of each of the first sections 112 is disposed adjacent the outer peripheral surface 108. In another embodiment of a retention member 300, shown in FIG. 7, the first sections 312 of the retention member 300 may assume a rectangular shape. It is contemplated that the first sections 112 may assume other shapes not illustrated herein, such as, for example, circular, oblong, or any suitable shape.

With continued reference to FIGS. 3-5, each of the first sections 112 includes a bottom surface 120 and a transition surface 122. The bottom surface 120 of each of the first sections 112 is coplanar or substantially coplanar with the upper and lower surfaces 104, 106 of the retention member 100. The transition surface 122 may assume a curved or flat configuration and partially or completely surrounds the bottom surface 120. The transition surface extends transversely or obliquely between the bottom surface 120 of the first section 112 and the upper surface 104 of the retention member 100. In embodiments, the transition surface 122 may extend perpendicularly relative to the upper and lower surfaces 104, 106 of the retention member 100. The transition surface 122 facilitates a smooth entry of an endoscope or other surgical instrument through the opening 102 of the retention member 100.

Figure 8:
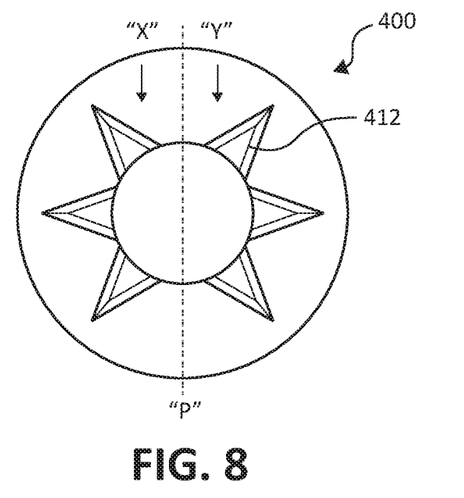
FIG. 8 is a top view of yet another embodiment of a retention member for receipt in the obturator assembly of FIG. 1.

In yet another embodiment of a retention member 400, shown in FIG. 8, the first sections 412 may be isolated into first and second groups "X" and "Y" rather than be spaced equidistantly. In particular, the first group "X" is disposed on a first side of a plane "P" extending perpendicularly through a center of the retention member 400, and the second group "Y" is disposed on a second side of the plane "P."

The operation of the optical trocar system 10 and, specifically the obturator assembly 11 will now be described. The obturator assembly 11 of the optical trocar system 10 is inserted through the cannula assembly 30 of the optical trocar system 10. The assembled optical trocar system 10 is positioned within an initial incision and against targeted tissue, e.g., an abdominal lining. A surgical instrument, such as an endoscope (not shown), is inserted through the obturator housing assembly 12 of the obturator assembly 11 and, in turn, the opening 102 of the retention member 100.

Due to the first sections 112 of the retention member 100 having a reduced thickness relative to the main body 101 thereof, the opening 102 in the retention member 100 dilates to accommodate the endoscope, whereby the inner peripheral surface 110 of the retention member 100 forms a friction fit with an outer surface of the endoscope. Advancement of the endoscope through the retention member 100 is continued to position a distal viewing end of the endoscope against the chamfered surface of the transparent optical member 20. Upon the endoscope being positioned at the desired location within the optical trocar system 10, the thicker main body 101 of the retention member 100 resists a change in the angular orientation of the endoscope within the obturator assembly 11.

Figure 9:
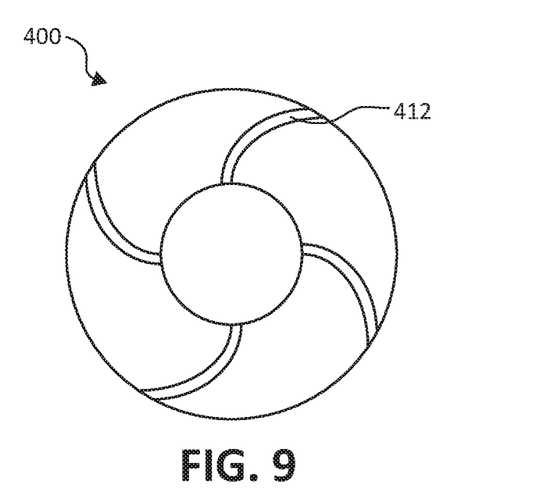
FIG. 9 is a top view of yet another embodiment of a retention member for receipt in the obturator assembly of FIG. 1.

With reference to FIG. 9, another embodiment of a retention member 400 is illustrated, similar to the retention members described above. The retention member 400 of the present embodiment differs from those above by having a plurality of reduced-thickness portions 412 that spiral from a center of the retention member 400.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. An obturator assembly including:
   an obturator housing defining a cavity therein;
   an obturator shaft extending distally from the housing; and
   a retention member disposed within the cavity of the obturator housing, the retention member including:
   a main body having a first thickness and including an upper surface, a lower surface, an annular-shaped, outer peripheral surface extending between the upper and lower surfaces, and an annular-shaped, inner peripheral surface extending between the upper and lower surfaces, the inner peripheral surface defining an opening through the main body dimensioned for receipt of a surgical instrument, the inner peripheral surface having a lower edge and the outer peripheral surface having a lower edge that is coplanar with the lower edge of the inner peripheral surface; and
   a plurality of first sections formed in the main body and circumferentially disposed about the opening, each section of the plurality of first sections having a second thickness that is less than the first thickness of the main body to facilitate flexing of the retention member during insertion of a surgical instrument into the opening, wherein the inner peripheral surface has a thickness defined between the upper and lower surfaces of the main body that alternates between the first and second thicknesses along a circumference of the inner peripheral surface.

2. The obturator assembly according to claim 1, wherein each section of the plurality of first sections extends radially outward from the opening.

3. The obturator assembly according to claim 1, wherein each section of the plurality of first sections extends from the inner peripheral surface of the main body of the retention member radially outward toward an outer peripheral surface of the main body of the retention member.

4. The obturator assembly according to claim 3, wherein each section of the plurality of first sections has an outer edge disposed inwardly of the outer peripheral surface.

5. The obturator assembly according to claim 3, wherein each section of the plurality of first sections has an outer edge coincident with the outer peripheral surface.

6. The obturator assembly according to claim 1, wherein each section of the plurality of first sections includes:
   a bottom surface; and
   a transition surface extending transversely between the bottom surface and one of the upper surface or the lower surface of the main body of the retention member.

7. The obturator assembly according to claim 1, wherein at least one first section of the plurality of first sections has a triangular configuration or a squared configuration.

8. The obturator assembly according to claim 1, wherein each section of the plurality of first sections is a depression formed in the upper surface or the lower surface of the main body of the retention member.

9. The obturator assembly according to claim 8, wherein the upper and lower surfaces of the main body of the retention member are planar.

10. The obturator assembly according to claim 1, wherein the retention member has a circular configuration.

11. The obturator assembly according to claim 1, wherein the opening is aligned with a central longitudinal axis defined by the obturator shaft.

12. The obturator assembly according to claim 1, wherein the retention member is fabricated from a unitary piece of elastic material.

13. The obturator assembly according to claim 12, wherein the elastic material includes at least one of rubber or silicone.

14. An optical trocar system, comprising:
   an obturator assembly including:
      an obturator housing defining a cavity therein;
      an obturator shaft extending distally from the housing; and
      a retention member disposed within the cavity of the obturator housing, the retention member including:
      a main body having a first thickness and including an upper surface, a lower surface, an annular-shaped outer peripheral surface extending between the upper and lower surfaces, and an annular-shaped, inner peripheral surface extending between the upper and lower surfaces, the inner peripheral surface defining an annular opening through the main body dimensioned for receipt of a surgical instrument, the inner peripheral surface having a lower edge and the outer peripheral surface having a lower edge that is coplanar with the lower edge of the inner peripheral surface; and
      a plurality of first sections formed in the main body and circumferentially disposed about the opening, each section of the plurality of first sections having a second thickness that is less than the first thickness of the main body to facilitate flexing of the retention member during insertion of a surgical instrument into the opening, wherein the inner peripheral surface has a thickness defined between the upper and lower surfaces of the main body that alternates between two different thicknesses along a circumference of the inner peripheral surface; and
   a cannula assembly configured to receive the obturator shaft of the obturator assembly therein.

15. The optical trocar assembly according to claim 14, wherein each section of the plurality of first sections extends radially outward from the opening.

16. The optical trocar assembly according to claim 15, wherein each section of the plurality of first sections is a depression formed in the upper surface or the lower surface of the main body of the retention member.

17. The optical trocar assembly according to claim 14, wherein each section of the plurality of first sections extends from the inner peripheral surface of the main body of the retention member radially outward toward an outer peripheral surface of the main body of the retention member.

18. The optical trocar assembly according to claim 17, wherein each section of the plurality of first sections has an outer edge disposed inwardly of the outer peripheral surface.

19. The optical trocar assembly according to claim 14, wherein at least one first section of the plurality of first sections has a triangular configuration or a squared configuration.

20. The optical trocar assembly according to claim 14, wherein the retention member is fabricated from a unitary piece of elastic material.

* * * * *